United States Patent [19]

Farnham

[11] Patent Number: 5,563,235
[45] Date of Patent: Oct. 8, 1996

[54] PROCESS FOR MAKING FLUORINATED ALDEHYDES

[75] Inventor: William B. Farnham, Hockessin, Del.

[73] Assignee: E. I. Du Pont de Nemours and Company, Wilmington, Del.

[21] Appl. No.: 587,353

[22] Filed: Jan. 16, 1996

Related U.S. Application Data

[62] Division of Ser. No. 388,017, Feb. 14, 1995, Pat. No. 5,512,652, which is a division of Ser. No. 823,211, Jan. 21, 1992, Pat. No. 5,414,140.

[51] Int. Cl.⁶ ........................................... C08G 10/02
[52] U.S. Cl. ..................... 528/244; 528/247; 568/448; 568/449; 568/490; 568/495; 525/402
[58] Field of Search ........................ 568/490, 448, 568/449, 495; 528/244, 247; 525/402

[56] References Cited

U.S. PATENT DOCUMENTS

| | | | |
|---|---|---|---|
| 2,568,500 | 9/1951 | Husted et al. | 260/601 |
| 2,828,287 | 3/1958 | Cairns et al. | 260/67 |
| 3,067,173 | 12/1962 | Barney | 260/63 |
| 3,208,975 | 9/1965 | Vandenberg | 260/67 |
| 3,398,123 | 8/1968 | Howard | 528/244 |

FOREIGN PATENT DOCUMENTS

3640178A1  6/1988  Germany.

OTHER PUBLICATIONS

J. D. Citron, *J. Org. Chem.*, 34, 1977–1979, 1969.
J. D. Citron, *J. Org. Chem.*, 36, 2547–2548, 1971.
K. Neeld et al., *J. Polym. Sci. Macromol Rev.*, 16, 1–40, 1981.

*Primary Examiner*—Jeffrey C. Mullis
*Assistant Examiner*—Terressa M. Mosley

[57] ABSTRACT

Fluorinated aldehydes are made by reacting a fluorinated acyl chloride with a silicon hydride in the presence of palladium. Also disclosed are fluorinated ether aldehydes and their polymers, a process for making fluorinated aldehydes polymers using titanium or aluminum alkoxide catalysts, and a process for endcapping fluorinated polymers using perfluoroallyl fluorosulfate or fluorine.

12 Claims, No Drawings

PROCESS FOR MAKING FLUORINATED ALDEHYDES

This is a division of Ser. No. 08/388,017, filed on Feb. 14, 1995 now U.S. Pat. No. 5,512,652, which was a division of Ser. No. 07/823,211, filed on Jan. 21, 1992 now U.S. Pat. No. 5,414,140.

FIELD OF INVENTION

This invention concerns a process for the manufacture of fluorinated aldehydes by the palladium catalyzed reaction of a silicon hydride with a fluorinated acyl chloride. Also disclosed are perfluorinated ether aldehydes and their polymers, a process for polymerizing fluorinated aldehydes, and processes for endcapping fluorinated aldehyde polymers.

BACKGROUND OF THE INVENTION

Fluorinated aldehydes and their polymers are known in the art, see for example U.S. Pat. No. 2,568,500, of Husted et al. issued Sep. 18, 1951; U.S. Pat. No. 2,828,287 of Cairns et al. issued Mar. 25, 1958, and a review article on fluoroaldehyde polymers, K. Neeld and O. Vogl., J. Polym. Sci., Macromol. Rev., vol. 16, p. 1–40 (1981). Fluorinated aldehydes form polymers that are useful as chemically and thermally resistant elastomers and thermoplastics, useful for making parts that require these-properties, and for films and coatings. Fluorinated aldehydes have been made by a variety of methods.

U.S. Pat. No. 3,067,173 of Barney issued Dec. 4, 1962, discloses various halogenated polyacetals. These polymers contain halogenated β-alkoxy groups. β-alkoxypolyfluoroaldehydes are used in their preparation.

J. D. Citron, J. Org. Chem., vol. 34, p. 1977–1979 (1969), reports that acyl chlorides react with silicon hydrides in the presence of palladium to form aldehydes. No mention is made of the formation of fluorinated aldehydes.

German Patent 3,640,178 A1 published Jun. 6, 1988 describes the synthesis of fluorosubstituted aldehydes by the reaction of fluoroacyl fluorides with silicon hydrides in the presence of palladium or a palladium complex. The use of fluoroacyl chlorides is not mentioned.

J. D. Citron, J. Org. Chem., vol. 36, p. 2547–2548 (1971) reports that acyl fluorides do not react with silicon hydrides in the presence of palladium. However, a reaction to produce an ester does occur when an acyl fluoride and a silicon hydride are heated together.

U.S. Pat. No. 3,208,975 reports that various chelated aluminum compounds, some of which contain alkoxides, catalyze the polymerization of various aldehydes, including trifluoroacetaldehyde. No mention is made of using aluminum compounds containing fluorinated alkoxides.

This invention provides a process for making fluorine substituted aldehydes from available starting materials, particularly making them sufficiently pure so as to be readily polymerizable. This invention also provides novel fluorinated aldehydes and their polymers, a process for making fluorinated aldehyde polymers, and a method for endcapping fluorinated aldehyde polymers.

SUMMARY OF THE INVENTION

This invention provides a process for the production of fluorinated aldehydes, comprising, contacting finely divided palladium, a silicon hydride of the formula $(R^5)_3SiH$, and an acyl chloride of the formula

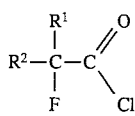

wherein:

$R^1$ is fluorine, perfluoroaryl or $R^3R^4CF$—;

$R^2$ is fluorine, perfluoroaryl

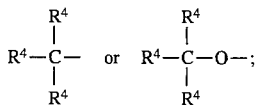

$R^3$ and each $R^4$ are independently fluorine, hydrocarbyl, or substituted hydrocarbyl; and each $R^5$ is independently alkyl, to yield a fluorinated aldehyde of formula

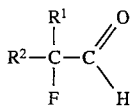

wherein:

$R^1$ and $R^2$ are as defined above.

This invention also comprises an aldehyde of the formula $$Y(CX_2CX_2O)_k(C_3F_6O)_m(CF_2O)_n(CX_2)_pCF_2CHO$$

wherein:

Y is fluorine, aryloxy or —$OCF{=}CF_2$;

each X is independently hydrogen or fluorine;

p is 0 or 1; and k, m and n are each independently zero or an integer of 1 to 50; provided that k+m+n is 2 or more.

This invention also comprises a polymer, comprising the repeat unit

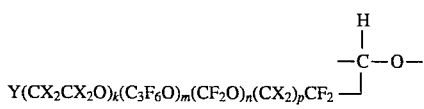

wherein:

Y is fluorine, aryloxy or —$OCF{=}CF_2$;

each X is independently hydrogen or fluorine;

p is 0 or 1; and k, m and n are each independently zero or an integer of 1 to 50; provided that k+m+n is 2 or more.

This invention also provides a process for the polymerization of fluorinated aldehydes comprising contacting an aldehyde of the formula ACHO with a titanium (IV) compound or an aluminum (III) compound in which one or more alkoxy groups are bound to the titanium or aluminum atom, wherein:

A is perfluoroaryl or $R^6R^7FC$—;

$R^6$ is fluorine, perfluoroaryl, perfluoroalkyl, or ether substituted perfluoroalkyl; and $R^7$ is fluorine, hydrogen or substituted alkyl; provided that the initial molar ratio of said aldehyde to said titanium or aluminum compound is no more than about 50,000 to 1, and further provided that for the aluminum compound, the alkoxide groups each contain at least one fluorine atom.

This invention also provides a process for endcapping a fluorinated aldehyde polymer comprising contacting a fluorinated aldehyde polymer, which is capable of further polymerization, with perfluoroallyl fluorosulfate or fluorine, provided that when endcapping with perfluoroallyl fluorosulfate the polymer is formed by anionic polymerization.

DETAILS OF THE INVENTION

This invention concerns a process for the preparation of an aldehyde of the formula

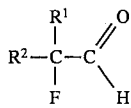

comprising contacting an acyl chloride of the formula

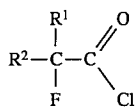

with a silicon hydride of the formula $(R^5)_3SiH$ in the presence of finely divided palladium wherein $R^1$, $R^2$, and $R^5$ are as defined above. The silicon hydride reacts with the acyl chloride, reducing the acyl chloride to the corresponding aldehyde.

In a preferred acyl chloride (and in the product aldehyde) $R^1$ is fluorine. In another preferred acyl chloride $R^1$ is $R^3R^4CF—$, and $R^2$ and $R^3$ are fluorine; it is more preferred if in addition $R^4$ is perfluoroalkyl; and especially preferred if $R^4$ is perfluoro-n-alkyl. In another preferred acyl chloride $R^2$ is fluorine and $R^1$ is $R^3R^4CF—$ wherein $R^3$ is fluorine and $R^4$ is $CF_3—$, n-$C_5F_{11}—$, $CF_2=CFOCF_2CF(CF_3)O—$, $CF_3CH_2OCF_2CHFOCF_2CF(CF_3)O—$, or $CF_3CH_2O—$. In another preferred embodiment $R^1$ is $R^3R^4CF—$ wherein $R^3$ and $R^4$ are both fluorine, and $R^2$ is $CF_3CF_2CF_2O—$. A preferred perfluoroaryl group is pentafluorophenyl.

Substituted hydrocarbyl includes, but is not limited to linear, branched or cyclic alkyl, alkenyl, alkynyl, dienyl, or aryl of 1 to 20 carbon atoms substituted with one or more of ether, fluorine, chlorine, bromine, cyano and alkoxycarbonyl substituents. Preferred substituents are fluorine and ether, and fluorine is especially preferred. When ether oxygens are present, they are present between carbon atoms in the acyl chloride (and product aldehyde).

The silicon hydride, $(R^5)_3SiH$, reduces the acyl chloride to the fluorinated aldehyde. In preferred silicon hydrides, each $R^5$ contains 1 to about 20 carbon atoms, preferably 1 to 4 carbon atoms. In preferred silicon hydrides, every $R^5$ is isopropyl or ethyl, and isopropyl is more preferred.

The palladium metal used in the process is present in finely divided form. Usually, and preferably, it will be on a support such as carbon (charcoal). Carbon is a preferred support. Such supported metals are well known to those skilled in the art and are commercially available. A preferred concentration is about 2 to 10% by weight of the metal on the support. Finely divided palladium metal may be made according to the process described in J. D. Citron, et al., J. Org. Chem., vol. 34, p. 638–640 (1969).

The process of the present invention can be carried out in the presence of an inert solvent, such as a fluorohydrocarbon solvent, however, it is preferred to carry out the process in the absence of solvent. Some types of compounds that may act as solvent can complex with fluorinated aldehydes, but fluorinated aldehydes are best polymerized when they are not complexed. It is sometimes difficult to isolate the fluorinated aldehyde from its complexes, so a solventless process which produces pure fluorinated aldehyde is preferred.

The process of the present invention is conducted at any convenient temperature at which the starting materials and products are stable. However, it is preferred that the process temperature be about −20° C. to about +50° C., preferably about −10° C. to about 30° C. The process is conducted at ambient pressure.

The presence of compounds containing active hydrogen atoms, such as water (moisture), alcohols, primary and secondary amines, etc., should be avoided, since these compounds may react with the acyl chloride and/or silicon hydride, and may also complex with the fluorinated aldehyde product. A convenient way to exclude these materials is to use an inert atmosphere, such as nitrogen or argon.

Although not necessary, it is preferred to agitate the process mixture to speed the reaction. The product slurry contains the palladium, chlorosilane, and fluorinated aldehyde. The desired aldehyde may be obtained by filtering or distilling the organic compounds from the palladium, and then distilling or separating the resulting mixture of chlorosilane and fluorinated aldehyde to obtain the pure aldehyde. Such a procedure permits no contact with compounds that may Complex the fluorinated aldehyde. Other methods of isolating the fluorinated aldehyde will be apparent to the art skilled and are also illustrated in the Examples.

Although almost any molar ratio of silicon hydride to acyl chloride may be used, in order to use the ingredients most efficiently, an approximately 1:1 molar ratio is preferred, although sometimes a small excess (up to about 25%) of silicon hydride will give a slightly better yield. The ratio of palladium to the other reactants is not critical, about 0.001–0.01 gram atoms of palladium per mole of acyl chloride being a convenient range.

The process of the present invention is useful in making fluorinated aldehydes. The fluorinated aldehydes made by the instant invention are useful as monomers for making polymers. The resultant polymers are useful in films and coatings, particularly where solvent and heat resistance is required.

Also included in the present invention is an aldehyde of the formula

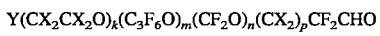

wherein p is 0 or 1; each X is independently hydrogen or fluorine; Y is fluorine, aryloxy or $—OCF=CF_2$; and k, m and n are each independently zero or an integer of 1 to 50; provided that k+m+n is 2 or more. The aldehydes can be prepared using the above described process of palladium catalyzed reaction of a silicon hydride with a fluorinated acyl chloride. Specific details are exemplified herein in Examples 6, 8 and 11. The fluorinated acyl chlorides are prepared from acyl fluorides as described below under the section titled "Starting Material Preparations". The acyl fluorides can be made by methods described in U.S. Pat. Nos. 3,665,041 and 4,664,766. The aldehydes are useful to prepare polymers useful as chemically and thermally resistant elastomers and thermoplastics, employed in making parts that require these properties, and for films and coatings.

The aldehydes described in the immediately preceding paragraph are polymerized to form polymers comprising the repeat unit

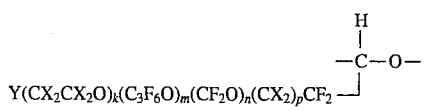

wherein p is an integer of 0 or 1; Y is fluorine, aryloxy or —CF=CF$_2$; each X is independently fluorine or hydrogen; and k, m and n are each independently zero or an integer of 1 to 50; provided that k+m+n is 2 or more. These polymers are made as described below for the polymerization of fluorinated aldehydes by contacting the aldehyde with a titanium (IV) compound or an aluminum (III) compound substituted with one or more alkoxy groups, or by other methods known to those skilled in the art, see for instance,. K. Neeld and O. Vogl, J. Polym. Sci., Macromol. Rev., vol. 16,. p. 1–40 (1981), which is hereby incorporated by reference. Specific details are exemplified in Examples 8–12 herein. These polymers are homopolymers containing only the above enumerated repeat unit, or are copolymers containing the above repeat unit with repeat units derived from other aldehydes. These polymers are useful as chemically and thermally resistant elastomers and thermoplastics, useful for making parts that require these properties, and for films and coatings.

This invention also provides a process for the polymerization of fluorinated aldehydes comprising contacting an aldehyde of the formula ACHO with a titanium (IV) compound or an aluminum (III) compound in which one or more alkoxy groups are bound to the titanium or aluminum atom, and wherein: A is perfluoroaryl or R$^6$R$^7$FC—; R$^6$ is fluorine, perfluoroaryl, perfluoroalkyl, or ether substituted perfluoroalkyl; and R$^7$ is fluorine, hydrogen or substituted alkyl. This polymerization may be carried out with or without solvent present, but it is preferred if solvent is absent. Suitable solvents include, but are not limited to, ether, chlorofluorocarbons, and hydrofluorocarbons.

The polymerization is carried out at about –50° C. to about 75° C., preferably 0° C. to 50° C., and more preferably about 10° C. to 30° C. The process ingredients should be dry, and care should be taken to exclude moisture, as by performing the polymerization under an inert gas such as nitrogen. For best results, the monomer should be stored at less than 0° C. before use, preferably in a polytetrafluoroethylene container. The polymer may be isolated by evaporation of the solvent and other volatiles, or if solid, by filtration.

The initial molar ratio of aldehyde to metal alkoxide is from about 50,000 to 1 to about 50 to 1, preferably from about 10,000 to 1 to about 100 to 1, and more preferably from about 5,000 to 1 to about 250 to 1.

The titanium (IV) and aluminum (III) compounds used in the process have at least one alkoxy group bound to the metal atom. The alkoxy group may be substituted with various substituents such as chloro, bromo, cyano, fluoro, ether and other inert substituents. Fluoro is a preferred substituent for the alkoxy group in the titanium compound and is required in each alkoxy group in the aluminum compound. The presence of fluorine in the alkoxy groups makes the polymerization catalyst more soluble in highly fluorinated aldehydes, and gives smoother polymerizations. The titanium compound may have one to four alkoxy groups, but one is preferred. When there are less than four alkoxy groups other ligands that can form stable bonds to titanium (IV) may be present, such as a triethanolamine ligand [N(CH$_2$CH$_2$O—)$_3$]. By titanium (IV) is meant titanium the +4 state. Preferred alkoxy groups for the titanium compounds are isopropoxide, CF$_3$CH$_2$O—, (CF$_3$)$_2$CHO—, and CF$_2$=CFOCF$_2$CF(CF$_3$)OCF$_2$CF$_2$CH$_2$O—. A preferred alkoxy group for the aluminum compound is CF$_3$CH$_2$O—.

Preferred is the polymerization process wherein the titanium (IV) compound is GTiJ wherein G is isopropoxide, CF$_3$CH$_2$O—, (CF$_3$)$_2$CHO—, or CF$_2$=CFOCF$_2$CF(CF$_3$)OCF$_2$CF$_2$CH$_2$O—, and J is N(CH$_2$CH$_2$O—)$_3$.

This process using a titanium or aluminum alkoxide to polymerize a fluorinated aldehyde results in rapid polymerization of the aldehyde to form essentially linear polymers. These linear polymers are useful as chemically and thermally resistant elastomers and thermoplastics, for making parts requiring these properties, and for films and coatings.

This invention also provides a process for endcapping a fluorinated aldehyde polymer comprising contacting a fluorinated aldehyde polymer which is capable of further polymerization, with perfluoroallyl fluorosulfate or fluorine, provided that when endcapping with perfluoroallyl fluorosulfate the polymer is formed by anionic polymerization. It is well known that polymers of aldehydes, particularly fluorinated aldehydes, tend to "unzip" or depolymerize to monomers under a variety of conditions, including thermally, and acid and base catalysis. In order to isolate the polymers of fluorinated aldehydes before unzipping takes place, it is preferred to "endcap" the polymer with a group that prevents unzipping. The choice of endcapping group will affect the thermal stability of the polymer.

Thus endcapping is carried out on a fluorinated aldehyde polymer which is capable of further polymerization. By that is means that the group on the end of the polymer causes further polymerization if more aldehyde is added. This group is sometimes referred to as the polymer living end. In addition when perfluoroallyl fluorosulfate is used to endcap the polymer, the polymer is formed by anionic polymerization. Anionic polymerization includes the use of catalysts such as fluoride ion, fluorosilicates, and alkali metal alkoxides. Endcapping with perfluoroallyl fluorosulfate or fluorine gives polymers that are relatively thermally stable.

The endcapping may be carried out at any temperature at which the reactants are stable, but it is preferably carried out at about 0° C. to about 30° C., which is the temperature at which the fluorinated aldehydes are typically polymerized. The perfluoroallyl fluorosulfate or fluorine is simply added to and mixed with the polymerization mixture after the polymer is formed. No compound which reacts with perfluoroallyl fluorosulfate or fluorine should be present in the polymerization mixture other than the polymer ends.

Typical times for complete endcapping are about 1 to 24 hr with perfluoroallyl fluorosulfate. In order to ensure complete endcapping it is preferred to use a large excess of the perfluoroallyl fluorosulfate, at least about 100 moles of the fluorosulfate per mole of polymer to be endcapped. Lesser ratios may be used, but longer reaction times and/or incomplete capping may result. Due to the end cap derived from the perfluoroallyl fluorosulfate or fluorine, the resulting endcapped polymers are also included in the present invention.

When using fluorine to endcap the polymer, usually a mixture of fluorine and an inert gas such as nitrogen will be used, for example 80 volume percent nitrogen and 20 volume percent fluorine, at a pressure of about 1×10$^5$ to 13×10$^5$ Pa. Fluorine resistant reactors, such as those made of Hastelloy®, should be used. After the reaction is complete, excess fluorine and other byproducts can be removed by washing with sodium bicarbonate solution. It is preferred if the endcapping with fluorine is done without added solvent.

In the Examples the following abbreviations are used:

DSC—differential scanning calorimetry
F11—fluorotrichloromethane
F113—1,1,2-trichloro-1,2,2,-trifluoroethane
glyme—1,2-dimethoxyethane
Mn—number average molecular weight
MW—molecular weight
Mw—weight average molecular weight
TASF—tris(dimethylaminosulfonium)t-
   rimethyldifluorosilicate
TGA—hermogravimetric analysis
THF—tetrahydrofuran
Starting Material Preparations

PREPARATION OF $CF_3CF_2CF_2OCF(CF_3)COCl$

A mixture of $AlCl_3$ and o-dichlorobenzene (4 mL) was treated with $CF_3CF_2CF_2OCF(CF_3)COF$ (13.2 g, 40 mmol) and heated at 6 °C. for 0.5 hr. Volatiles were removed by vacuum transfer (27 Pa) to give a mixture of two liquids. The lower layer was separated and distilled to provide 8.0 g of colorless liquid, bp ca. 65° C. GC analysis showed 99% purity. $^{19}F$ NMR (F11): −81.32 (s, $CF_3$), −81.94 (t, J=7.3 Hz, $CF_3$), −79.05 and −84.98 (AB pattern, J=146 Hz, $OCF_2$), −126.1 (d of m's, J=23, CF), −130.1 (s, $CF_2$).

PREPARATION OF $CF_3CH_2OCF_2CF_2C(O)OCH_3$, $CF_3CH_2OCF_2CF_2C(O)ONa$, AND $CF_3CH_2OCF_2CF_2C(O)OK$

The methyl ester was prepared according to the method described in literature: Krespan et al., J. Am. Chem. Soc., 106, 5544 (1984), which is hereby incorporated by reference.

The sodium and potassium salts of the acid were prepared according to procedures described by E. D. Laganis and B. L. Chenard, Tetrahedron Letters, 25, 5831 (1984), which is hereby incorporated by reference.

PREPARATION OF $CF_3CH_2OCF_2CF_2C(O)Cl$

A 3-necked round bottom flask fitted with a reflux condenser and mechanical stirrer was charged with $CF_3CH_2OCF_2CF_2C(O)OK$ (14.2 g, 50 mmol). Oxalyl chloride (6.34 g, 50 mmol) was added dropwise at a rate suitable to control the exotherm and evolution of gas. When gas evolution had ceased, the mixture was heated at 80° C. for 1.0 hr. Volatiles were removed under vacuum (27 Pa) to give 12.1 g of colorless liquid (93%) homogeneous by GC. IR ($CCl_4$): 1803 cm$^{-1}$ (C=O) $^1H$ NMR ($CD_2Cl_2$): 4.42 (q, J=7.5 Hz). $^{19}F$ NMR: −74.85 (tt, 7.7, 2.3, $CF_3$), −87.1 (m, $OCF_2$), −116.27 (t, J=4.5, $CF_2$). GC/MS featured observed m/z at 199.0028; calcd. for $C_4H_2OF_7$ (M-C(O)Cl)= 198.9994.

PREPARATION OF $CF_3CH_2OCF_2CHFOCF_2CF(CF_3)OCF_2CF_2C(O)OCH_3$

Oil-free sodium hydride (150 mg) was treated with DMF (30 mL) and cooled to 0° C. Trifluoroethanol (10.9 g, 110 mmol) was added, and the mixture was allowed to warm to 25° C. A 30.0 g (71 mmol) sample of $CF_2=CFOCF_2CF(CF_3)OCF_2CF_2CO_2CH_3$ was added. GC analysis revealed that little reaction had occurred, so an additional 2.2 mL of trifluoroethanol and 0.2 g sodium hydride dispersion were added. After the exotherm subsided, the mixture was stirred for 6 hr, poured into water (150 mL), neutralized with HCl, and extracted with 1,1,2-trichloro-1, 2,2-trifluoroethane. The organic layer was washed four times with water, dried, and stripped to give 52.2 g of residue. Kugelrohr distillation provided 34.6 g, bp 44°–54° C./7 Pa (94%). $^1H$ NMR (THF-$d_8$): 6.72 (d of m's, J=52 Hz), 4.63 (q, J=8), 3.97 (s). $^{19}F$ NMR: −74.77 (t, J=8.2, $CF_3$), −79.99 and −80.83 (overlapping t, J=9), −82.0 to −85.3 (overlapping AB patterns, 4F), −90.0 and −90.5 (AB pattern, J=149), −121.35 (m), −145.0 (m), −145.87 (d of m's), consistent with the desired ester.

PREPARATION OF $CF_3CH_2OCF_2CHFOCF_2CF(CF_3)OCF2CF2C(O)OK$

A suspension of potassium trimethyl silanoate (9.6 g, 75 mmol) in ether (150 mL) was treated with $CF_3CH_2OCF_2CHFOCF_2CF(CF_3)OCF_2CF_2C(O)OCH_3$ (39.5 g, 76 mmol) prepared as described above and the mixture was stirred for 18 hr. Since the product was quite soluble, the solvent was removed under vacuum to give 40.4 g of white solid. $^1H$ NMR (acetone-$d_6$): 6.80 and 6.83 (d of t's, $J_d$=52, $J_t$=3.4 for two diastereomers), 4.71 and 4.70 (overlapping quartets, J=8.5). $^{19}F$ NMR: −74.2 (t, J=8.4), −79.3 (m), −80.5 to −85.5 (overlapping AB's), −89.4 (center of overlapping AB patterns), −118.13 and −118.19 ($CF_2CO_2$ singlets), −144.5 to −145.7 (overlapping m's), consistent with the desired structure.

PREPARATION OF $CF_3CH_2OCF_2CHFOCF_2CF(CF_3)OCF_2CF_2C(O)Cl$

A 3-necked round bottom flask equipped with a reflux condenser, nitrogen inlet, and mechanical stirrer was charged with $CF_3CH_2OCF_2CHFOCF_2CF(CF_3)OCF_2CF_2C(O)OK$ (37.9 g, 69 mmol) prepared as described above. Oxalyl chloride (8.8 g, 69 mmol) was added dropwise at a rate to maintain the temperature below ca. 35° C. and to allow for gas evolution. When the addition was complete, the mixture was heated to 80° C. for 1.25 hr. Volatiles were transferred under vacuum (13 Pa) while the pot was maintained at 80° C. Product was purified by spinning band distillation (17 mm) to give 29 g of desired acid chloride, obtaining 16.8 g as a center cut with bp 78° C. $^1H$ NMR ($CDCl_3$): 5.98 (d of t's, J=52, 3.5 Hz), 4.32 (q, J=8 Hz). $^{19}F$ NMR: ($CD_2Cl_2$/F11): −75.08 (t, J=7.9), −80.3 (m), −81.6 (m), overlapping AB patterns −83.44 and −85.74 (J=145) and −83.77 and −86.08 (J=150), −90.01 and −90.88 (AB pattern, J=143, with small shift differences for the diastereomers), −116.5 (overlapping doublets, J=3.5), −145.1 (m, overlapping signals for tertiary CF and CHF moieties).

EXAMPLE 1

PREPARATION OF $C_7F_{15}CHO$

A sample of triethylsilane (4.24 g, 36.5 mmol) was cooled to 0° C. and treated with 10% Pd/C (0.35 g). After the exotherm subsided, perfluorooctanoyl chloride (15.8 g, 36.5 mmol) was added dropwise, controlling the temperature below ca. 6°–8° C. The mixture was stirred for 1.0 hr at 0° C. Another 0.59 g triethylsilane was added, and the mixture was stirred for 1.5 hr. An additional 0.13 g of triethylsilane was added. After 1.0 hr, vacuum transfer gave 16.4 g of liquid which was cooled at −250°C. for several hours. The top liquid layer was removed from the solid to provide ca. 10.5 g of the titled product. $^{19}F$ NMR: −81.3 (t of t's, J=9.8, 2.3), −121.8 (m), −122.3 (m), −123.0 (m), 123.7 (m), −125.4 (t of m's, with $J_{FCCH}$=3 Hz ), −126.5 (m).

EXAMPLE 2

PREPARATION OF $C_7F_{15}CHO$

Catalyst 10% Pd/C (200 mg) was placed in a 3-necked round bottom flask and cooled at 0° C. Triisopropylsilane (3.32 g, 21 mmol) was added, followed by perflurooctanoyl chloride (7.9 g, 18.2 mmol). The mixture was allowed to warm to room temperature and was then controlled at 25°–27° C. during the exothermic reaction. After 3 hr, GC analysis showed aldehyde/acid chloride ratio=94/6. Another 0.26 mL of silane was added and stirring was continued for 1 hr. Vacuum transfer gave liquid which was chilled at −25° C. The resulting solid was shaken with petroleum ether, chilled at −25° C., and separated again. In this way, 6.48 g of product was obtained, mp ca. −5° C. NMR spectra were as described in Example 1.

EXAMPLE 3

PREPARATION OF $C_3F_7CHO$

A 3-necked round bottom flask fitted with with dropping funnel, dry-ice condenser, and gas inlet was charged with 10% Pd/C (0.35 g) and cooled to 0° C. Triisopropylsilane (7.29 g, 46 mmol) was added, and $CF_3CF_2CF_2C(O)Cl$ (9.30 g, 40 mmol) was added dropwise over a 10 min period. The reactor was connected to a cold trap (−78° C.) while the mixture was stirred for 18 hr. Transfer from the trap and reaction vessel gave a total of 5.1 g (62%) of colorless liquid. $^1$H NMR ($CD_2Cl_2$): 9.62 (m). $^{19}$F NMR: −81.24 (t, J=8.3 Hz), −126.4 (quartet of doublets, $J_q$=8.3, $J_d$=3.2), −127.9 (s).

EXAMPLE 4

PREPARATION OF $CF_3CF_2CF_2OCF(CF_3)CHO$

A 3-necked round bottom flask equipped with a dropping funnel and reflux condenser was charged with 10% Pd/C (0.35 g) and cooled to 0° C. Triisoprolpylsilane (6.0 g) was added. $CF_3CF_2CF_2OCF(CF_3)COCl$ (10.9 g) was added, and the mixture was stirred at 25° C. for 75 hr. During this period, a total of 0.5 g of additional catalyst was added in ca. 0.1 g increments. Vacuum transfer and separation of the lower layer after chilling at −25° C. provided 5.26 g of liquid. $^1$H NMR (THF-$d_8$/F11): 9.9 (m). $^{19}$F NMR: −79.4 (m), −81.1 (s), −81.4 (t, J=7.2), −129.5 (s), −138.8 (m). $^1$H-decoupling experiment showed $J_{HCCF}$ ca. 2.5 Hz.

EXAMPLE 5

PREPARATION OF $CF_2=CFOCF_2CF(CF_3)OCF_2CF_2CHO$

A 3-necked round bottom flask equipped with addition funnel and condenser was charged with 10% Pd/C (0.53 g) and cooled in an ice bath. Triisopropylsilane (8.1 g, 51 mmol) was added, and $CF_2=CFOCF_2CF(CF_3)OCF_2CF_2COCl$ (17.3 g, 41 mmol) was added dropwise over 25 min. The mixture was warmed to 25° C. and the exotherm was controlled by a 25° C. water bath. The mixture was stirred for 18 hr, and product was transferred from the reactor at 67 Pa. The liquid so obtained was chilled at −25°C. and the lower layer was separated and washed several times with petroleum ether. Layer separations were carried out at ca. −20° C. to −25° C. There was obtained 7.9 g (4% isolated) of desired product. $^{19}$F NMR ($C_6D_6$/F11) −80.3 (m, $CF_3$), −82.2 (m, $OCF_2$), −85.0 (m, $OCF_2$), −113.5 (dd, J=66, 83 Hz, vinyl CF), −121.9 (dd of triplets, $J_t$=5.1, $J_d$=83, 113 Hz, vinyl CF), −127.6 (d, J=2.3, $CF_2CHO$), −135.8 (d of d's of t's, $J_t$=5.7, $J_d$=66, 112, vinyl CF), −145.1 (t, J=22, CF). IR ($CCl_4$) featured bands at 1768 and 1837 cm$^{-1}$.

EXAMPLE 6

PREPARATION OF $CF_3CH_2OCF_2CF_2CHO$

A 3-necked round bottom flask was charged with 10% Pd/C (400 mg) and cooled to 0° C. Triisopropylsilane (6.44 g, 40.7 mmol) was added, and $CF_3CH_2OCF_2CF_2COCl$ (9.15 g, 34.9 mmol) was added dropwise. The mixture was warmed to room temperature, and the exotherm was then controlled by a room temperature water bath. The mixture was stirred an additional 22 hr over which time an additional 0.2 g of catalyst was added. The product was removed by vacuum transfer at 27 Pa. After isolation of the lower layer and washing several times with petroleum ether at −25° C., there was obtained 4.32 g of colorless liquid. $^{19}$F NMR (glyme-$d_{10}$): −74.4 (t of t'2, J=8.2, 2.7), −87.35 (m, $OCF_2$), −128.27 (apparent quartet, J=4 Hz, $CF_2CHO$). GC/MS showed the major product with a fragment ion of m/z= 209.0023. Calcd. for $C_5H_3F_6O_2$ (M-F): 209.0037.

EXAMPLE 7

PREPARATION OF $CF_3CH_2OCF_2CHFOCF_2CF(CF_3)OCF_2CF_2CHO$

A 3-necked round bottom flask equipped with an addition funnel was charged with 10% Pd/C (1.2 g) and cooled to 0° C. Triisopropylsilane. (11.0 g, 70 mmol) was added in one portion and $CF_3CH_2OCF_2CHFOCF_2CF(CF_3)OCF_2CF_2COCl$ (30 g, 57 mmol) was added dropwise over a 10 min period. The mixture was allowed to warm to ca. 25° C., and the exotherm was controlled by a cool water bath. Conversion of the acid chloride was substantially complete at this stage. The last few percent was converted to product by addition of 0.3 g Pd/C and 1.8 g triisopropylsilane and stirring for 48 hr. Product was removed at 13 Pa while maintaining the reaction vessel at ca. 40°–50° C. The lower layer was isolated after chilling at −25°C., and additional washing with petroleum ether gave 16.5 g of colorless liquid. $^1$H NMR (THF-$d_8$): 9.64 (m), 6.72 (d of m's, J=52), 4.62 (q, J=8). $^{19}$F NMR: −74.80 (t, J=8, $CF_3CH_2$), −80.0 (m, $CF_3$), −81.7 to −85.3 (overlapping AB patterns, $OCF_2$), −89.95 and −90.64 (AB patterns, J=145, $OCF_2$), −127.91 (apparent quartet, J=2.5, $CF_2CHO$), −144.7 (apparent t, J=21, CF), −145.9 (d of m's, J=52, CHF). IR ($CCl_4$) featured bands at 1768 cm$^{-1}$ (C=O) and 1240–1150 cm$^{-1}$ (CF). GC/MS showed highest mass fragment of m/z=471.9844. Calcd. for $C_{10}H_3F_{15}O_4$ (M-H, F) =471.9791.

EXAMPLE 8

POLYMERIZATION OF $CF_3CH_2OCF_2CF_2CHO$ WITH TASF IN THF

A sample of the title aldehyde (0.63 g) was treated with a solution of TASF, tris(dimethylaminosulfonium)trimethyldifluorosilicate, (4 mg) in THF (2 mL) and cooled to −25° C. for ca. 10 min. After warming to 25° C., NMR analysis (dilution with THF-$d_8$) revealed a 40/60 mixture of polymer/monomer. Further addition of catalyst resulted in similar solution viscosity, but slow evaporation of solvent provided a soft gel. Size exclusion analysis of the crude product showed a faction (20%) of material with $\overline{M}_n$=236,000, the remainder of low molecular weight. Thus in THF solution, TASF treatment of this monomer results in slow reaction and incomplete conversion of monomer.

EXAMPLE 9

POLYMERIZATION OF $CF_3CH_2OCF_2CHFOCF_2CF(CF_3)OCF_2CF_2CHO$ WITH TASF

A catalyst solution was prepared by treating TASF, tris-(dimethylaminosulfonium)trimethyldifluorosilicate, (10 mg) with 10 drops of 1,1,2,2,3,3-hexafluorocylcopentane. One drop of the catalyst solution was added to the title aldehyde (0.50 g) and the mixture was manipulated with a spatula. After 18 hr, perfluoroallylfluorosulfate (1.0 mL) was added and the mixture was stirred for 1.5 hr. 1,1,2-trichloro-1,2,2-trifluoroethane (10 mL) was added, and stirring was continued for ca. 1.5 hr to afford a viscous solution. After an additional 1.5 hr, volatiles were removed and product was washed with $CH_2Cl_2$ to give 0.46 g of white waxy solid. TGA showed a 10% weight loss between 150° C. and 230° C., then a more rapid loss. DSC featured Tg at −53° C. Size exclusion analysis showed: $\overline{M}_w$=395,000; $\overline{M}_n$33,500. $^{19}$F NMR (THF-d$_8$): −75.0 (bd s, $CF_3CH_2$), −80.0 and −80.2 ($CF_3$+part of $OCF_2$), −82.5 to −87.0 (bd, overlapping signals, $OCF_2$), −90.8 (bd s, $OCF_2$), −121 to −126 and −132 to −139 (bd, overlapping collection of AB patterns for $CF_2CH$), −145.0 (bd s, CF), and −146 (bd d of m's, CHF). $^1$H NMR (THF-d$_8$): 6.5 (d of m's, J=52 Hz, CHF), 5.8 and 5.4 (bd, overlapping signals), 4.5 (bd m, $CH_2CF_3$).

EXAMPLE 10

POLYMERIZATION OF $C_7F_{15}CHO$ WITH $CF_3CH_2OTiL_3$

Alkoxytitaniumtriethanolamine complexes were prepared as described below. A solution of titanium isopropoxide (28.4 g, 0.1 mol) in toluene (100 mL) was treated with triethanolamine (freshly distilled, 14.9 g). After 3 hr at ambient temperature, the solvent was removed under reduced pressure, and the product was triturated with ether, then filtered and washed with small amounts of ether to provide 23.5 g of white powder (93%), mp 111°–113° C. Anal. calcd. for $C_9H_{19}O_4NTi$: C, 42.70; H, 7.57; N, 5.53. Found: C, 42.18; H, 7.18; N, 5.55. $^1$H NMR ($CD_2Cl_2$): 4.60 (sept, J=6, CH), 4.40 (t, J=5.6, $CH_2$), 3.15 (t, J=5.6, $CH_2$), 1.20 (d, J=6.0, $CH_3$).

A mixture of the above triethanolaminetitanium isopropoxide (9.29 g, 36.7 mmol) and toluene (100 mL) was treated with trifluoroethanol (7.34 g, 73.4 mmol) and was stirred for 67 hr. The resulting suspension was evaporated, and the solid was triturated with ether and filtered to give 10.08 g of white powder, mp 177°–180° C. $^{19}$F NMR ($CD_2Cl_2/25°$ C.): −76.5 (t, J=9), $^1$H NMR: 4.70 (q, J=10 Hz), 4.57 (m, $CH_2$), and 3.30 (m, $CH_2$). Spectra were temperature-dependent.

A sample of $C_7F_{15}CHO$ (400 mg) was treated with the title titanate (4 mg). The resulting mixture gelled and then became a crumbly white solid. TGA showed the onset of weight loss at ca. 65° C.

EXAMPLE 11

POLYMERIZATION OF $CF_3CH_2OCF_2CF_2CHO$ WITH $EVEOTiL_3$ $EVEOTiL_3$, ($CH_2$=$CFOCF_2CF(CF_3)OCF_2CF_2CH_2OTi(OCH_2CH_2)_3N$), was prepared as follows: A mixture of triethanolaminetitanium isopropoxide (2.53 g, 10 mmol) and toluene (20 mL) was treated with $CH_2$=$CFOCF_2CF(CF_3)OCF_2CF_2CH_{20}H$ (3.94 g, 10 mmol) and stirred for 24 hr at 25° C. The solvent was removed under reduced pressure, and the gummy solid (6.0 g) was triturated with petroleum ether, filtered and washed with more petroleum ether. $^{19}$F NMR ($CD_2Cl_2$): −80.0 (m, $CF_3$), −83.7 (center of AB pattern, $OCF_2$), −84.8 (center of AB pattern, $OCF_2$), −113.55 (dd, J=65, 84 Hz, CF), −121.7 (dd of m's, J=84, 112, CF), −122.3 (bd s, $CF_2CH_2$), −135.6 (dd of triplets, J=65, 112, 5.7, CF), −145.2 (t, J=22, CF).

A sample of $CF_3CH_2OCF_2CF_2CHO$ (1.0 g, 4.39 mmol) in a small vial was treated with $EVEOTiL_3$ (4 mg) and stirred until a gel formed. After 18 hr, a hard, white solid was formed. Since depolymerization occurred in solution, NMR and size exclusion analyses were carried out as soon as possible after product was dissolved in THF. In both, starting aldehyde was clearly evident, and signals due to this component increased with time. $^{19}$F NMR: −74.35 (bd s), −85.23 and −87.57 (bd AB pattern, J=140 Hz, $OCF_2$), −123.0 and −136.7 (bd AB pattern, J=282 Hz). Size exclusion analysis showed a broad distribution of molecular weights ranging from ca. $1.2\times10^6$ to 1100.

EXAMPLE 12

POLYMERIZATION OF FLUORINATED ALDEHYDE WITH TITANIUM ISOPROPOXIDE

A sample of $C_7F_{15}CHO$ (1.00 g, 2.59 mmol) was treated with titanium isopropoxide (4.0 µL, $1.4\times10^{-2}$ mmol) by syringe. The liquid was mixed and allowed to stand for 0.5 hr. The resulting solid was manipulated with a spatula and allowed to stand for 0.3 hr. The $^{19}$F NMR spectrum of the product, recorded without solvent (after melting at 130° C.): −82.7 (brd s, $CF_3$), −121.7, −122.0, and −123.0 (singlets, 3 $CH_2$ groups), −124.0 (s, $CF_2$), and −126.6 (s, 2 $CF_2$) was consistent with a single type of $C_7F_{15}$ fragment. Starting material and characterizable ends were not observed.

EXAMPLE 13

POLYMERIZATION OF $CF_3CH_2OCF_2CHFOCF_2CF(CF_3)OCF_2CF_2CHO$ WITH $Al(OCH_2CF_3)_3$

Aluminum trifluoroethoxide was prepared by treatment of a toluene solution of triethylaluminum (0.38M) with these equivalents of trifluoroethanol at −25° C. After gas evolution was complete, the reaction mixture was allowed to stand at room temperature. When precipitation of product appeared to be well-advanced (1–2 hr), the reaction mixture was cooled at −25° C. for 18 hr before collecting the solid product. From 1.76 mmol of $Et_3Al$ and 0.528 g trifluoroethanol was obtained 435 mg of white solid, mp 171°–172° C. $^1$H NMR (THF-d$_8$): 4.1 (q, J=8). $^{19}$F NMR (THF-d$_8$): −77.0 (bd s), trace signals at −76.3 and −77.7.

A sample of the title aldehyde (0.50 g) was treated with aluminum trifluoroethoxide (0.2 mg). The resulting solution formed a clear gel, and this was allowed to stand for 18 hr.

$^{19}$F NMR analysis showed that the product readily reverts to starting aldehyde in THF-$d_8$.

EXAMPLE 14

ENDCAPPING WITH FLUORINE

A 1.0 g sample of polyacetal obtained in a similar manner as Example 13 by reaction of $CF_2CH_2OCF_2CHFOCF_2CF(CF_3)OCF_2CF_2CHO$ and $Al(OCH_2CF_3)_3$ was cut in small pieces and placed in a Hastelloy® cylinder which was evacuated and then pressurized at $3.7\times10^5$ Pa with an 80/20 mixture of $N_2/F_2$. After 10 days, excess $F_2$ was removed and the solid was washed thoroughly with aqueous sodium bicarbonate to give 0.97 g of white solid. TGA analysis showed 20% weight loss between 120° and 275° C. Removal of the unstabilized material by heating under vacuum at 195° C. for 1.5 hr gave a white solid exhibiting good stability to 285° C. This material was not soluble. It exhibited a Tg at −50° C.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A compound comprising an aldehyde of the formula $$Y(CX_2CX_2O)_k(C_3F_6O)_m(CF_2O)_n(CX_2)_pCF_2CHO$$

wherein:

Y is fluorine, aryloxy or —OCF=CH$_2$;

each X is independently hydrogen or fluorine;

p is 0 or 1; and k, m and n are each independently zero or an integer of 1 to 50; provided that k+m+n is 2 or more.

2. A compound of claim 1 which is $CF_2=CFOCF_2CF(CF_3)OCF_2CF_2CHO$ or $CF_3CH_2OCF_2CHFOCF_2CF(CF_3)OCF_2CF_2CHO$.

3. A process for the polymerization of fluorinated aldehydes comprising contacting an aldehyde of the formula ACHO with a titanium (IV) compound or an aluminum (III) compound in which one or more alkoxy groups are bound to the titanium or aluminum atom, wherein:

A is perfluoroaryl or $R^6R^7FC$—;

$R^6$ is fluorine, perfluoroaryl, perfluoroalkyl, or ether substituted perfluoroalkyl; and $R^7$ is fluorine, hydrogen or substituted alkyl;

provided that the initial molar ratio of said aldehyde to said titanium or aluminum compound is no more than about 50,000 to 1, and further provided that for the aluminum compound, the alkoxide groups each contain at least one fluorine atom.

4. The process as recited in claim 3 wherein said temperature is from about −50° C. to about 75° C.

5. The process as recited in claim 3 wherein said molar ratio is from about 5,000 to 1 to about 250 to 1.

6. The process as recited in claim 3 wherein said alkoxy group for the titanium (IV) compound is isopropoxide, $CF_3CH_2O$—, $(CF_3)_2CHO$—, or $CF_2=CFOCF_2CF(CF3)OCF_2CF_2CH_2O$—.

7. The process as recited in claim 3 wherein said titanium (IV) compound is GTiJ, wherein G is isopropoxide, $CF_3CH_2O$—, $(CF_3)_2CHO$—, or $CF_2=CFOCF_2CF(CF_3)OCF_2CF_2CH_2O$—, and J is $N(CH_2CH_2O$—$)_3$.

8. The process as recited in claim 3 wherein said alkoxy group for the aluminum (III) compound is $CF_3CH_2O$—.

9. A process for endcapping a fluorinated aldehyde polymer comprising contacting a fluorinated aldehyde polymer, which is capable of further polymerization, with perfluoroallyl fluorosulfate or fluorine, provided that when endcapping with perfluoroallyl fluorosulfate the polymer is formed by anionic polymerization.

10. The process as recited in claim 9 which is carried out at a temperature of from about 0° C. to about 30° C.

11. The process as recited in claim 9 wherein the molar amount of said perfluoroallyl fluorosulfate is about 100 times or more of the molar amount of polymer to be endcapped.

12. The product of the process of claim 9.

* * * * *